(12) United States Patent
Niitsu et al.

US010570396B2

(10) Patent No.: US 10,570,396 B2
(45) Date of Patent: Feb. 25, 2020

(54) CELL DEATH INDUCING AGENT FOR CELLS HAVING BRAF GENE MUTATION, GROWTH SUPPRESSING AGENT FOR SAME CELLS AND PHARMACEUTICAL COMPOSITION FOR THERAPY OF DISEASES CAUSED BY GROWTH DEFECT OF SAME CELLS

(71) Applicant: Nitto Denko Corporation, Osaka (JP)

(72) Inventors: Yoshiro Niitsu, Sapporo (JP); Hiroki Nishita, Osaka (JP)

(73) Assignee: Nitto Denko Corporation, Ibaraki-shi, Osaka (JP)

( * ) Notice: Subject to any disclaimer, the term of this patent is extended or adjusted under 35 U.S.C. 154(b) by 0 days.

(21) Appl. No.: 15/567,062

(22) PCT Filed: Apr. 15, 2016

(86) PCT No.: PCT/JP2016/062090
§ 371 (c)(1),
(2) Date: Oct. 16, 2017

(87) PCT Pub. No.: WO2016/167340
PCT Pub. Date: Oct. 20, 2016

(65) Prior Publication Data
US 2018/0135058 A1 May 17, 2018

(30) Foreign Application Priority Data
Apr. 16, 2015 (JP) ................ 2015-084286
Apr. 11, 2016 (JP) ................ 2016-078710

(51) Int. Cl.
*C07H 21/04* (2006.01)
*C12N 15/113* (2010.01)
*G01N 33/50* (2006.01)

(52) U.S. Cl.
CPC ...... *C12N 15/1137* (2013.01); *G01N 33/5011* (2013.01); *C12N 2310/14* (2013.01); *G01N 2500/10* (2013.01)

(58) Field of Classification Search
None
See application file for complete search history.

(56) References Cited

U.S. PATENT DOCUMENTS

2014/0315975 A1 10/2014 Niitsu
2015/0328248 A1 11/2015 Niitsu

FOREIGN PATENT DOCUMENTS

WO WO 2015/001345 A1 1/2015

OTHER PUBLICATIONS

Cho, Nam-Yun, et al. "BRAF and KRAS mutations in prostatic adenocarcinoma." International journal of cancer 119.8 (2006): 1858-1862.*
Zhang, mTOR Signaling is Involved in Indomethacin and Nimesulide Suppression of Colorectal Cancer Cell Growth via a COX-2 Independent Pathway, Ann Surg Oncol, 2011, vol. 18, pp. 580-588.
Mertens, Oral Indomethacin and Ranitidine in Advanced Melanoma: A Phase II Study, Clinical Oncology, 1996, vol. 8, pp. 112-115.
Tsai, Discovery of a selective inhibitor of oncogenic B-Raf kinase with potent antimelanoma activity, Proc. of the National Academy Sciences of the USA, 2008, vol. 105, pp. 3041-3046.
Extended European Search Report dated Nov. 19, 2018 for the European Patent Application No. 16780131.5.
Nishita, Regulation of autophagy and MAPK signaling by glutathione S-transferase-pi in KRAS mutated cancer cells, AACR 102nd Annual Meeting, Cellular and Molecular Biology, Proceedings of the Amer Assoc for Cancer Res, 2011, vol. 52, p. 257, Abstract #1065.
Pratilas, Targeting Oncogenic BRAF in Human Cancer, Current Topics in Microbiology, 2012, vol. 355, pp. 83-98.
Halilovic, Therapeutic strategies for inhibiting oncogenic BRAF signaling, Current Op in Pharmacology, 2008, vol. 8, pp. 419-426.
Phipps, KRAS-mutation status in relation to colorectal cancer survival: the joint impact of correlated tumour markers, British J of Cancer, 2013, vol. 108, pp. 1757-1764.
Ban, Transfection of Glutathione S-Transferase (GST)-p' Antisense Complementary DNA Increases the Sensitivity of a Colon Cancer Cell Line to Adriamycin, Cisplatin, Melphalan, and Etoposide, Cancer Res, 1996, vol. 56, pp. 3577-3582.
Nakajima, Reversal of Multiple Drug Resistance in Cholangiocarcinoma by the Glutathione S-Transferase-p-Specific Inhibitor O1-Hexadecyl-g-glutamyl-S-benzylcysteinyl-D-phenylglycine Ethylester, J of Pharmacol and Experimental Therapeutics, 2003, vol. 306, pp. 861-869.
Hokaiwado, Glutathione S-transferase Pi mediates proliferation of androgen-independent prostate cancer cells, Carcinogenesis, 2008, vol. 29, pp. 1134-1138.
Adler, Regulation of JNK signaling by GSTp, The EMBO Journal, 1999, vol. 18 No. 5 pp. 1321-1334.
Townsend, Novel Role for Glutathione S-Transferase-pi, J of Biological Chem, 2009, vol. 284, pp. 436-445.
Yin, Glutathione S-Transferase p Elicits Protection against H2O2-induced Cell Death via Coordinated Regulation of Stress Kinases, Cancer Res, 2000, vol. 60, pp. 4053-4057.
Darr, BRAF V600E status predicts higher uPA levels in papillary thyroid cancer, AACR 102nd Annual Meeting, Cellular and Molecular Biology, Proceedings of the Amer Assoc for Cancer Res, 2011, vol. 52, p. 257.
De Luca, A novel orally active water-soluble inhibitor of human glutathione transferase exerts a potent and selective antitumor activity against human melanoma xenografts, Oncotarget, 2015, vol. 6, pp. 4126-4143.
Turley, GSTP1 Supression Induces Apoptosis in Melanoma Cells Independent of BRAF Mutational Status, J of Surgical Res, 2012, vol. 172, pp. 229, Abstract 21.6.
Fedyanin M. et al., Promises for treating colon cancer patients with *BRAF*gene mutation. Oncological Coloproctology (2014) 3:9-16; [retrieved online URL: https://cyberleninka.ru/article/n/perspectivy-lecheniya-bolnyh-rakom-tolstoy-kishki-s-mutatsiey-v-gene-braf].
Shao Y. et al., BH3-only protein silencing contributes to acquired resistance to PLX4720 in human melanoma. Cell Death Differ. (2012) 19(12):2029-2039.
Russian Office Action/Search Report dated Oct. 1, 2019 for Application No. 2017139718, filed Apr. 15, 2016 (21 pages).

* cited by examiner

*Primary Examiner* — Kimberly Chong
(74) *Attorney, Agent, or Firm* — Knobbe, Martens, Olson & Bear LLP

(57) ABSTRACT

Cell death is induced and/or cell growth is suppressed for a cell having a mutation in the BRAF gene. A drug suppressing GST-π is comprised as an active ingredient.

11 Claims, 6 Drawing Sheets
Specification includes a Sequence Listing.

(a)

(b)

CELL DEATH INDUCING AGENT FOR CELLS HAVING BRAF GENE MUTATION, GROWTH SUPPRESSING AGENT FOR SAME CELLS AND PHARMACEUTICAL COMPOSITION FOR THERAPY OF DISEASES CAUSED BY GROWTH DEFECT OF SAME CELLS

TECHNICAL FIELD

The present invention relates to a cell death inducing agent for a cell having a BRAF gene mutation (for example, a type of cancer cell), a growth suppressing agent for the same cell and a pharmaceutical composition for therapy of a disease caused by a growth defect of the same cell, and further relates to a method for screening for the cell death inducing agent and/or the cell growth suppressing agent.

BACKGROUND ART

BRAF gene is a gene encoding a type of serine threonine kinase constituting the RAS-RAF-MAPK pathway. Mutations in BRAF gene have been reported in various tumors. For example, the mutation wherein the valine at amino acid 600 is substituted with glutamic acid (V600E) is found in many cancer cells. BRAF having the V600E mutation is known to always activate the downstream signaling and cause a cell growth without extracellular stimulation.

For example, the BRAF gene having the V600E mutation is found in many colorectal cancers (5 to 15%) and melanoma (about 60%). Note that, in many cancers such as pancreatic cancer and colorectal cancer, mutations in a KRAS gene are found at high frequency. The KRAS protein is G proteins locally present on the inner surface of cell membrane. RAS such as KRAS activates RAF such as CRAF and BRAF, RAF sequentially activates MEK and MEK activates MAPK, thus forming a cascade (Non Patent Literatures 1 and 2). It is a rare case to contain both BRAF mutation and KRAS mutation as the BRAF mutation and the KRAS mutation are in the mutually exclusive relationship (Non Patent Literature 3).

Currently, for cancers with BRAF having the V600E mutation, a therapy by an inhibitor against BRAF having the V600E mutation is considered effective. Vemurafenib (PLX4032) and PLX4720 are known as such an inhibitor. However, cancer cells may acquire the resistance to these inhibitors by the continuous administration thereof which makes the therapy effects limited. Thus, for cancer cells having a mutation in the BRAF gene, more effective cell death inducing agents and growth suppressing agents replacing these inhibitors have been in demand.

Glutathione-S-transferase (GST), one of the enzymes catalyzing the glutathione conjugation, is known as an enzyme conjugating a substance such as a drug with glutathione (GSH) into an aqueous substance. GST is, based on the amino acid sequence, classified representatively into 6 types of the isozyme, $\alpha$, $\mu$, $\omega$, $\pi$, $\theta$ and $\zeta$. Of these, the expression of GST-$\pi$ (glutathione S-transferase pi, also referred to as GSTP1) particularly has been increasing in various cancer cells and is indicated to have been a possible factor of the resistance to some anticancer agents. In fact, it is known that when an antisense DNA or a GST-$\pi$ inhibitor against GST-$\pi$ is allowed to act on a drug resistant cancer cell system overexpressing GST-$\pi$, the drug resistance is suppressed (Non Patent Literatures 4 to 6). Further, in a recent report, when siRNA against GST-$\pi$ is allowed to act on a GST-$\pi$ overexpressing androgen-independent prostatic cancer cell line, the growth thereof is suppressed and the apoptosis is increased (Non Patent Literature 7).

Additionally, GST-$\pi$ is known to form a complex with c-Jun N-terminal kinase (JNK) and inhibit the JNK activity (Non Patent Literature 8). Further, GST-$\pi$ is known to be involved with the S-glutathionylation of proteins associating with the cell stress responses (Non Patent Literature 9). Furthermore, GST-$\pi$ is known to contribute to the protective action on the cell death induced by reactive oxygen species (ROS) (Non Patent Literature 10). As described above, GST-$\pi$ among GST is understood to have various features and functions.

It is reported that when siRNA against GST-$\pi$ is allowed to act on a cancer cell system having a KRAS mutation, Akt activation is suppressed and autophagy increases but the apoptosis induction is about moderate (Non Patent Literature 11). Patent Literature 1 discloses that cancer cell apoptosis can be induced using a drug suppressing GST-$\pi$ and an autophagy inhibitor such as 3-methyladenine as active components. Patent Literature 2 further discloses that when the expression of GST-$\pi$ and Akt is simultaneously inhibited, the cell growth is suppressed and the cell death is induced and the autophagy induced by the GST-$\pi$ expression inhibition is notably suppressed by simultaneously inhibiting the expression of Akt and the like.

However, in the cell having a mutation in the BRAF gene described above, there is no finding in the relationship between the expression of GST-$\pi$ and the cell growth or the cell death or the role of GST-$\pi$ in the signal transduction.

CITATION LIST

Patent Literature

Patent Literature 1: WO2012/176282
Patent Literature 2: WO2014/098210

Non Patent Literature

Non Patent Literature 1: Curr Top Microbiol Immunol. 2012; 355: 83-98
Non Patent Literature 2: Curr Opin Pharmacol. 2008 August; 8(4): 419-26.
Non Patent Literature 3: British Journal of Cancer (2013) 108, 1757-1764.
Non Patent Literature 4: Takahashi and Niitsu, Gan To Kagaku Ryoho. 1994; 21(7): 945-51
Non Patent Literature 5: Ban et al., Cancer Res. 1996; 56(15): 3577-82
Non Patent Literature 6: Nakajima et al., J Pharmacol Exp Ther. 2003; 306(3): 861-9
Non Patent Literature 7: Hokaiwado et al., Carcinogenesis. 2008; 29(6): 1134-8
Non Patent Literature 8: Adler et. al, EMBO J. 1999, 18, 1321-1334
Non Patent literature 9: Townsend, et. al, J. Biol. Chem. 2009, 284, 436-445
Non Patent literature 10: Yin et. al, Cancer Res. 2000 60, 4053-4057
Non Patent literature 11: Nishita et al., AACR 102nd Annual Meeting, Abstract No. 1065

SUMMARY OF INVENTION

Technical Problem

Under the circumstances, the present invention has an object to provide an agent having a cell death inducing action and/or a cell growth suppressing action for a cell having a mutation in the BRAF gene, provide a pharmaceutical composition for therapy of a disease caused by a cell growth defect and provide a method for screening for the cell death inducing agent and/or the cell growth suppressing agent.

Solution to Problem

The present inventors conducted extensive studies in view of the above object and found that the cell growth is intensively suppressed when GST-π is suppressed in a cell having a mutation in the BRAF gene and the cell growth is also intensively suppressed when GST-π is suppressed even in a cell having the BRAF gene mutation and resistant to the conventionally known BRAF inhibitors, whereby the present invention was accomplished. The present invention includes the following.

(1) A cell death inducing agent for a cell having a mutation in a BRAF gene, comprising a drug suppressing GST-π as an active ingredient.

(2) A cell growth suppressing agent for a cell having a mutation in a BRAF gene, comprising a drug suppressing GST-π as an active ingredient.

(3) The agent according to (1) or (2), wherein the mutation is V600E mutation.

(4) The agent according to (1) or (2), wherein the cell having a mutation in a BRAF gene is a cell resistant to a BRAF inhibitor.

(5) The agent according to (1) or (2), wherein the drug is a substance selected from the group consisting of RNAi molecules, ribozymes, antisense nucleic acids, DNA/RNA chimera polynucleotides and vectors expressing at least one thereof.

(6) The agent according to (1) or (2), wherein the cell having a mutation in a BRAF gene is a cancer cell highly expressing GST-π.

(7) A pharmaceutical composition for therapy of a disease caused by a growth defect of a cell having a mutation in a BRAF gene, comprising the agent according to any one of the above (1) to (6).

(8) The pharmaceutical composition according to (7), wherein the disease is a cancer.

(9) The pharmaceutical composition according to (8), wherein the cancer is a cancer highly expressing GST-π.

(10) The pharmaceutical composition according to (8), wherein the cancer is colorectal cancer or melanoma.

(11) A method for screening for a cell death inducing agent and/or a cell growth suppressing agent for a cell having a mutation in a BRAF gene, comprising selecting a drug suppressing GST-π.

(12) The method for screening according to (11) comprising a step of contacting a test substance with a cancer cell, a step of measuring an expression level of GST-π in the cell and a step of selecting the test substance as the drug suppressing GST-π when the expression level is reduced compared with a case measured in the absence of the test substance.

The present Description encompasses the disclosed contents described in Japanese Patent Application No. 2015-84286 and Japanese Patent Application No. 2016-78710, which are the basis of priority of the present application.

Advantageous Effects of Invention

According to the cell death inducing agent of the present invention, the cell death can be induced very intensively for a cell having a mutation in the BRAF gene. Accordingly, the cell death inducing agent of the present invention can render a very high efficacy as a pharmaceutical composition for therapy of a disease caused by a growth defect of a cell having a mutation in the BRAF gene.

Additionally, according to the cell growth suppressing agent of the present invention, the cell growth can be suppressed very intensively for a cell having a mutation in the BRAF gene. Accordingly, the cell growth suppressing agent of the present invention can render a very high efficacy as a pharmaceutical composition for therapy of a disease caused by a growth defect of a cell having a mutation in the BRAF gene.

Further, according to the method for screening according to the present invention, a drug for inducing the cell death and/or for suppressing the cell growth very intensively for a cell having a mutation in the BRAF gene can be selected.

DESCRIPTION OF EMBODIMENTS

Figure 1:
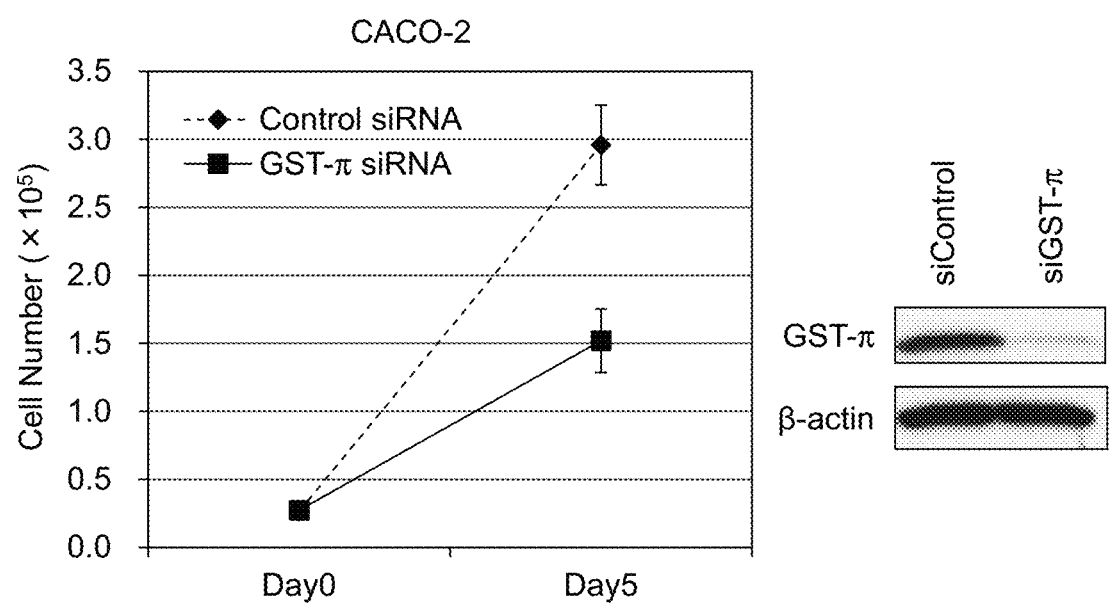
FIG. 1 is a characteristic diagram showing the verification results of cell growth suppressing effect due to GST-π knockdown in a colorectal cancer cell line having a mutation in the BRAF gene (cell number count results, Western blotting results).

The cell death inducing agent and the cell growth suppressing agent of the present invention comprise a drug suppressing GST-π as an active ingredient. The cell death inducing agent and the cell growth suppressing agent of the present invention demonstrate the cell death inducing effect and the cell growth suppressing effect for a cell having a mutation in the BRAF gene.

GST-π, when used in the present Description, refers to an enzyme which is encoded by GSTP1 gene and catalyzes the glutathione conjugation. GST-π is present in various animals including human and the sequence information thereof is known (for example, human: NM_000852 (NP_000843), rat: NM_012577 (NP_036709), mouse: NM_013541 (NP_038569), etc. The numbers represent NCBI database accession numbers, the numbers outside the parentheses are nucleotide sequences and the numbers in the parentheses are amino acid sequences.) As an example, the nucleotide sequence in a coding region of human GST-π gene registered in the database is set forth in SEQ ID NO: 1 and the amino acid sequence in human GST-π protein encoded by the human GST-π gene is set forth in SEQ ID NO: 2.

Note that GST-π can be specified by the specific nucleotide sequence and amino acid sequence as described above but a mutation in the nucleotide sequence and amino acid sequence (including polymorphisms) possibly caused between biological individuals must be considered. More specifically, GST-π is not limited to proteins having the identical sequence with the amino acid sequence registered in the database but includes those having the equal function to GST-π and having a sequence with 1 or 2 or more, typically 1 or several, for example, 1, 2, 3, 4, 5, 6, 7, 8, 9 or 10 different amino acids from the above sequence. Additionally, GST-π also include those consisting of a nucleotide sequence having 70% or more, 80% or more, 90% or more, 95% or more, or 97% or more, identity with the above specific nucleotide sequence and encoding a protein having the equal function to GST-π. Note that the specific function of GST-π, as described above, refers to the enzyme activity catalyzing the glutathione conjugation.

Note that, in the present Description, the phrases such as "when used in the present Description", "used in the present Description", "in the present Description" and "described in the present Description" mean that the subsequent descriptions to these phrases apply to all inventions described in the present Description unless otherwise stated. Additionally, unless otherwise defined, all technical terms and scientific terms used in the present Description have the same meaning to those commonly understood by those skilled in the art. All patents, patent publications and other publications cited herein shall be incorporated in entirety in the present Description.

Examples of the "drug suppressing GST-π" used in the present Description includes, but not limited thereto, drugs suppressing the production and/or activity of GST-π and drugs facilitating the decomposition and/or inactivation of GST-π. Examples of the drugs suppressing the production of GST-π include, but not limited thereto, RNAi molecules, ribozymes, antisense nucleic acids, DNA/RNA chimera polynucleotides to the DNA encoding GST-π and vectors expressing these.

Additionally, for the drug suppressing GST-π, any compounds which act on GST-π can be used. Examples of such usable compounds include organic compounds (amino acids, polypeptides or derivatives thereof, low-molecular weight compounds, carbohydrates and high-molecular weight compounds) and inorganic compounds. Further, these compounds may be natural substances or non-natural substances. Examples of the polypeptide derivative include modified polypeptides obtained by adding a modifying group and variant polypeptides obtained by varying an amino acid residue. Furthermore, these compounds may be a single compound or may be a chemical library, expression products of a gene library, cell extracts, cell culture supernatants, fermentation microorganism products, marine organism extracts and plant extracts. More specifically, the "drug suppressing GST-π" is not limited to nucleic acids such as RNAi molecules but include any compounds.

Specific examples of the drug suppressing the activity of GST-π include, but not limited thereto, substances conjugating GST-π such as glutathione, glutathione analogs (e.g., WO 95/08563, WO 96/40205, WO 99/54346 and those described in Non Patent Literature 4, etc.), ketoprofen (Non Patent Literature 2), indomethacin (Hall et al., Cancer Res. 1989; 49(22):6265-8), ethacrynic acid, piriprost (Tew et al., Cancer Res. 1988; 48 (13):3622-5), anti-GST-π antibodies and dominant negative mutants of GST-π. These drugs are commercially available or can be suitably produced based on known technologies.

The drug suppressing the production or activity of GST-π is preferably RNAi molecules, ribozymes, antisense nucleic acids, DNA/RNA chimera polynucleotides to the DNA encoding GST-π or vectors expressing these due to the high specificity and low chance of side effects.

The suppression of GST-π can be determined based on the GST-π expression or activity suppressed in a cell compared with the case where a GST-π inhibitor was not allowed to act on. The expression of GST-π can be evaluated by any known techniques such as, without any limitation, immunoprecipitation method utilizing an anti-GST-π antibody, EIA, ELISA, IRA, IRMA, Western blotting method, immunohistochemical method, immunocytochemical method, flow cytometry method, various hybridization methods, Nothern blotting method, Southern blotting method and various PCR methods in which a nucleic acid capable of specifically hybridizing to a nucleic acid encoding GST-π or a unique fragment thereof or a transcript (e.g., mRNA) or a spliced product of the nucleic acid.

The activity of GST-π can be evaluated by analyzing known GST-π activities such as, without any limitation, the bindability to proteins such as Raf-1 (particularly phosphorylated Raf-1) and EGFR (particularly phosphorylated EGFR) by any known methods such as immunoprecipitation method, Western blotting method, mass spectrometry, pull-down assay or surface plasmon resonance (SPR) method.

The RNAi molecule, when used in the present Description, refers to any molecules rendering RNA interference and includes, but not limited thereto, double stranded RNAs such as siRNA (small interfering RNA), miRNA (micro RNA), shRNA (short hairpin RNA), ddRNA (DNA-directed RNA), piRNA (Piwi-interacting RNA) and rasiRNA (repeat associated siRNA) and variants thereof. These RNAi molecules are commercially available or can be designed and manufactured based on known sequence information, more specifically, the nucleotide sequence as set forth in SEQ ID NO: 1 and/or the amino acid sequence as set forth in SEQ ID NO: 2. Additionally, the antisense nucleic acid, when used in the present Description, includes RNA, DNA, PNA and complexes thereof.

The DNA/RNA chimera polynucleotide, when used in the present Description, includes, but not limited thereto, double stranded polynucleotides consisting of DNA and RNA inhibiting the expression of a target gene as described in JP Patent Publication (Kokai) No. 2003-219893 A.

The amount of an active ingredient to be added to the agent or composition of the present invention may be an amount inducing the cell death such as apoptosis and/or suppressing the cell growth when the agent or composition is administered. Additionally, an amount not causing detrimental effects which outweighs the benefits gained from the administration is preferable. Such an amount is known or suitably determined by an in vitro test using cultured cells or a test on a model animal such as a mouse, a rat, a dog or a pig, and these test methods are well known by those skilled in the art. The apoptosis induction can be evaluated by various known techniques using the detection of phenomenon distinctive to the apoptosis such as DNA fragmentation, binding of annexin V to a cell membrane, changes in the mitochondrial membrane potential or activation of caspase or TUNEL staining. Further, the suppression of cell growth can be evaluated by various known techniques such as counting over-time viable cell numbers, measurement of the size, volume and weight of a tumor, measurement of a DNA synthesis amount, WST-1 method, BrdU (bromodeoxyuridine) method or 3H thymidine incorporation method. The amount of an active component to be added is variable depending on the medication form of the agent and composition. For example, when multiple units of the composition are used for a single administration, the amount of an active ingredient added to a single unit composition can be one of multiple equal units of the amount of the active ingredient required for a single administration. Such an amount to be added can be suitably adjusted by those skilled in the art.

Additionally, the addition of the drug suppressing GST-π as the active ingredient enables the production of the cell death inducing agent, cell growth suppressing agent, cell death inducing composition or cell growth suppressing composition.

Further, the drug suppressing GST-π used for the cell death induction or cell growth suppression can be provided. Furthermore, the method for inducing the cell death or the method for suppressing the cell growth comprising administering an effective amount of the drug suppressing GST-π can be provided.

Note that both of the above method of cell death induction such as apoptosis or the cell growth suppression may be in vitro methods or in vivo methods. Additionally, the drug for these methods is as already described above and the effective amount of the drug may be an amount which induces the cell death or suppresses the cell growth in a cell to which the drug is administered. Additionally, an amount not causing detrimental effects which outweighs the benefits gained from the administration is preferable. Such an amount is known or can be suitably determined, for example by an in vitro test using cultured cells and the like, and the test method is well known by those skilled in the art. The cell death induction or the cell growth suppression can be evaluated by various known techniques including those described above. The above effective amount, when the drug is administered to a specified cancer cell group, does not need to be the amount which always causes the cell death or the growth suppression to all cells in the cell group. For example, the above effective amount may be an amount which causes the apoptosis or growth suppression to 1% or more, 2% or more, 3% or more, 4% or more, 5% or more, 6% or more, 8% or more, 10% or more, 12% or more, 15% or more, 20% or more, or further 25% or more, of the cells in the above cell group.

The cell death inducing agent and the cell growth suppressing agent of the present invention act on a cell having a mutation in the BRAF gene. The cell having a mutation in the BRAF gene is a cell demonstrating a growth defect due to a mutation in the BRAF gene (typically, cancer cells).

Particularly, the cell death inducing agent and the cell growth suppressing agent of the present invention are preferably applied to a cell highly expressing GST-π (typically, a cancer cell highly expressing GST-π) among the cells demonstrating a growth defect due to a mutation in the BRAF gene. The cancer cell highly expressing GST-π used herein means a cell having a significantly higher expression level of GST-π compared with a normal cell among the cells having a mutation in the BRAF gene and demonstrating a cell growth defect. Note that the expression level of GST-π can be measured in accordance with a routine method such as RT-PCR or microarray.

The mutation in the BRAF gene means a mutation such as deletion, substitution, addition, insertion in an amino acid sequence of wild-type BRAF and a mutation in an expression control region of the BRAF gene. Note that the mutation in the BRAF gene herein is the so-called gain of function mutation. More specifically, the BRAF gene having a mutation (sometimes referred to as the mutant BRAF gene) include genes encoding mutant BRAF with increased serine threonine kinase activity caused by the mutation. Additionally, the mutant BRAF gene also includes those having a mutation in an expression control region and an increased expression level compared with the wild-type BRAF gene. More specifically, a cell expressing the mutant BRAF gene has a feature of constantly maintaining downstream signaling (e.g., signaling to MEK) from BRAF by expressing mutant BRAF or increasing the expression level of BRAF.

Examples of the mutant BRAF gene include genes encoding mutant BRAF wherein the valine encoded by codon 600 in the wild-type BRAF gene is substituted with glutamic acid (notated as V600E. Hereinafter referred to as same) such as V600D, V600G, V600K, V600M, V600R, V600L, G469A, G469V, D594N and V600insT (insertion of T).

The cell death inducing agent and the cell growth suppressing agent of the present invention capable of effectively inducing the cell death or suppressing the cell growth even for a cancer cell having a mutation in the BRAF gene are thus effective as components of a pharmaceutical composition for a disease caused by a growth defect of a cancer cell having a mutation in the BRAF gene. Additionally, the formulation of the drug suppressing GST-π as the active ingredient enables the production of the pharmaceutical composition for a disease caused by the growth defect of a cancer cell having a mutation in the BRAF gene. Further, a disease caused by the cell growth defect can be subjected to treatment and therapy by comprising the administration of an effective amount of the produced pharmaceutical composition to a subject in need thereof.

The pharmaceutical composition is effective to treat a disease cause by the growth defect of a cancer cell having a mutation in the BRAF gene. The disease caused by a cancer cell having a mutation in the BRAF gene is not limited and includes cancers highly expressing GST-π, and in many cases cancers having a mutation in the BRAF gene are encompassed in the cancer highly expressing GST-π.

Examples include, but not limited thereto, sarcomas such as fibrosarcoma, malignant fibrous histiocytoma, liposarcoma, rhabdomyosarcoma, leiomyosarcoma, angiosarcoma, Kaposi's sarcoma, lymphangiosarcoma, synovial sarcoma, chondrosarcoma and osteosarcoma, carcinomas such as eye cancer, thyroid cancer (papillary cancer), meninges cancer, brain tumor, pituitary cancer, salivary gland cancer, head and neck cancer, breast cancer, lung cancer (non-small cell cancer), esophagus cancer, gastric cancer, duodenal cancer, appendiceal cancer, colorectal cancer, rectal cancer, liver cancer, pancreatic cancer, gallbladder cancer, bile duct cancer, anal cancer, kidney cancer, ureteral cancer, bladder cancer, prostatic cancer, penile cancer, testis cancer, uterine cancer (endometrial cancer), ovarian cancer (ovarian serous cancer), vulvar cancer, vaginal cancer and skin cancer (malignant melanoma), and further leukemia and malignant lymphoma. Note that the "cancer" in the present invention includes epithelial malignant tumor and non-epithelial malignant tumor. The cancer in the present invention can be present in any part of the body including brain, head and neck, chest, limb, lung, heart, thymus gland, esophagus, stomach, small intestines (duodenum, jejunum, ileum), large intestines (colon, cecum, appendix, rectum), liver, pancreas, gallbladder, anus, kidney, ureter, bladder, prostate gland, penis, testis, uterus, ovary, vulva, vagina, skin, striated muscle, smooth muscle, synovial membrane, cartilage, bone, thyroid, adrenal gland, peritoneum, mesentery, bone marrow, blood, vascular system, lymph system such as lymph node and lymph fluid.

Particularly, the cell death inducing agent and the cell growth suppressing agent of the present invention can effectively induce the cell death or suppress cell growth even for a cell that has acquired the resistance to a BRAF inhibitor among the cells having a mutation in the BRAF gene. Accordingly, the cell death inducing agent or the cell growth suppressing agent of the present invention are effective as the component of a pharmaceutical composition for a disease caused by the growth defect of a cancer cell having a mutation in the BRAF gene and resistance to a BRAF inhibitor. Additionally, the formulation of the drug suppressing GST-π as the active ingredient enables the production of the pharmaceutical composition for a disease caused by the growth defect of a cancer cell having a mutation in the BRAF gene and the resistance to a BRAF inhibitor. Further, a disease caused by the cell growth defect can be treated and therapied by comprising the administration of an effective amount of the produced pharmaceutical composition to a subject in need thereof, that is a patient with a reduced therapy effect by a BRAF inhibitor.

The BRAF inhibitor used herein means a substance inhibiting the signal transduction from BRAF to the downstream, particularly the substance specifically inhibiting the signal transduction caused by the mutant BRAF having the gain of function mutation described above. Examples of the known BRAF inhibitor include Vemurafenib ((PLX4032), Cas No.: 918504-65-1, N-[3-[5-(4-chlorophenyl)-1H-pyrrolo[2,3-b]pyridine-3-carbonyl]-2,4-difluorophenyl]propane-1-sulfonamide) and PLX4720 (Cas No.: 918505-84-7, N-[3-(5-chloro-1H-pyrrolo[2,3-b]pyridine-3-carbonyl)-2,4-difluorophenyl]propane-1-sulfonamide).

Further, examples of the BRAF inhibitor include regorafenib, dasatinib, PLX-8394, BeiGene-283, PLX-3603, RG-7304 (CAS NO.: 213406-50-9), LY-3009120 (CAS NO.: 1454682-72-4), rebastinib (Cas. No.: 1020172-07-9), 1H-pyrazolo[3,4-b]pyridine-5-carboxamide analogues, ASN-003, Vemurafenib prodrug, N-(thiophen-2-yl) benzamide derivatives, DCB-R0237, REDX-04988, EBI-907, EBI-945, gossypin, nanolipolee-007, TEW-0201, miRNA-3157 and thiazole derivative (NMS-P186, NMS-P285, NMS-P349, NMS-P383, NMS-P396 and NMS-P730).

Furthermore, examples of the BRAF inhibitor include, in addition to the above, SB590885 (Cas No.: 405554-55-4, N,N-dimethyl-2-[4-[(4Z)-4-(1-nitroso-2,3-dihydroinden-5-ylidene)-5-(1H-pyridin-4-ylidene)-1H-imidazol-2-yl]phenoxy]ethanamine), B-Raf inhibitor 1 (Cas No.: 1093100-40-3, 1-N-(4-chlorophenyl)-6-methyl-5-N-[3-(7H-purin-6-yl)pyridin-2-yl]isoquinoline-1,5-diamine), B-Raf inhibitor 1 dihydrochloride (Cas No.: 1191385-19-9, 1-N-(4-chlorophenyl)-6-methyl-5-N-[3-(7H-purin-6-yl)pyridin-2-yl]isoquinoline-1,5-diamine; dihydrochloride), Dabrafenib (Cas No.: 1195765-45-7, N-[3-[5-(2-aminopyrimidin-4-yl)-2-tert-butyl-1,3-thiazol-4-yl]-2-fluorophenyl]-2,6-difluorobenzenesulfonamide), LGX818 (Cas No.: 1269440-17-6, methyl N-[(2S)-1-[[4-[3-[5-chloro-2-fluoro-3-(methanesulfonamido)phenyl]-1-propan-2-ylpyrazol-4-yl]pyrimidin-2-yl]amino]propan-2-yl]carbamate), HG6-64-1 (Cas No.: 1315329-43-1, see WO 2011/090738), PF-04880594 (Cas No.: 1111636-35-1, 3-[[4-[1-(2,2-difluoroethyl)-3-(1H-pyrrolo[2,3-b]pyridin-5-yl)pyrazol-4-yl]pyrimidin-2-yl]amino]propanenitrile), BRAF inhibitor (Cas No.: 918505-61-0, N-[2,4-difluoro-3-(5-pyridin-3-yl-1H-pyrrolo[2,3-b]pyridine-3-carbonyl)phenyl]propane-2-sulfonamide), B-Raf inhibitor (Cas No.: 1315330-11-0, N-[4-[(4-ethylpiperazin-1-yl)methyl]-3-(trifluoromethyl)phenyl]-4-methyl-3-[(6-methyl-7H-pyrrolo[2,3-d]pyrimidin-4-yl)oxy]benzamide), TAK-632 (Cas No.: 1228591-30-7), N-[7-cyano-6-[4-fluoro-3-[[2-[3-(trifluoromethyl)phenyl]acetyl]amino]phenoxy]-1,3-benzothiazol-2-yl]cyclopropanecarboxamide, AZ 628 (Cas No.: 878739-06-1, 3-(2-cyanopropan-2-yl)-N-[4-methyl-3-[(3-methyl-4-oxoquinazolin-6-yl)amino]phenyl] benzamide), RAF265 (Cas No.: 927880-90-8, 1-methyl-5-[2-[5-(trifluoromethyl)-1H-imidazol-2-yl]pyridin-4-yl]oxy-N-[4-(trifluoromethyl)phenyl]benzimidazol-2-amine), CEP-32496 (Cas No.: 1188910-76-0, 1-[3-(6,7-dimethoxyquinazolin-4-yl)oxyphenyl]-3-[5-(1,1,1-trifluoro-2-methylpropan-2-yl)-1,2-oxazol-3-yl]urea), GDC-0879 (Cas No.: 905281-76-7, 2-[4-[(1E)-1-hydroxyimino-2,3-dihydroinden-5-yl]-3-pyridin-4-ylpyrazol-1-yl]ethanol), sorafenib tosylate (Cas No.: 475207-59-1, 4-[4-[[4-chloro-3-(trifluoromethyl)phenyl]carbamoylamino]phenoxy]-N-methylpyridine-2-carboxamide; 4-methylbenzenesulfonic acid), dabrafenib mesylate (Cas No.: 1195768-06-9, N-[3-[5-(2-aminopyrimidin-4-yl)-2-tert-butyl-1,3-thiazol-4-yl]-2-fluorophenyl]-2,6-difluorobenzenesulfonamide; methanesulfonic acid), CEP-32496 hydrochloride (Cas No.: 1227678-26-3, 1-[3-(6,7-dimethoxyquinazolin-4-yl)oxyphenyl]-3-[5-(1,1,1-trifluoro-2-methylpropan-2-yl)-1,2-oxazol-3-yl]urea; hydrochloride) and sorafenib (Cas No.: 284461-73-0, 4-[4-[[4-chloro-3-(trifluoromethyl)phenyl]carbamoylamino]phenoxy]-N-methylpyridine-2-carboxamide).

The pharmaceutical composition of the present invention may be used in combination with other active ingredients other than the drug suppressing GST-π. The used in combination herein include, for example, the administration of other active ingredients as separate pharmaceutical preparations and the administration of other active ingredients in the form of a combination agent with at least one of other drugs. When other active ingredients are administered as separate pharmaceutical preparations, a preparation containing other active ingredients may be administered before other preparations, together with other preparations or after other preparations.

For such other active ingredients, the above BRAF inhibitors can be suitably used. Additionally, other active ingredients also include those effective to treat a target disease. For example, when a disease to be treated is a cancer, an anticancer agent can be used in combination. Examples of the anticancer agent include alkylating agents such as ifosfamide, nimustine hydrochloride, cyclophosphamide, dacarbazine, melphalan and ranimustine, antimetabolites such as gemcitabine hydrochloride, enocitabine, cytarabine-ocfosfate, cytarabine preparations, tegafur-uracil, tegafur-gimeracil-oteracyl potassium combination agents (for example, TS-1), doxifluridine, hydroxycarbamide, fluorouracil, methotrexate and mercaptopurine, antitumor antibiotics such as idarubicin hydrochloride, epirubicin hydrochloride, daunorubicin hydrochloride, daunorubicin citrate, doxorubicin hydrochloride, pirarubicin hydrochloride, bleomycin hydrochloride, peplomycin sulfate, mitoxantrone hydrochloride and mitomycin C, alkaloids such as etoposide, irinotecan hydrochloride, vinorelbine ditartrate, docetaxel hydrate, paclitaxel, vincristine sulfate, vindesine sulfate and vinblastine sulfate, hormone therapy agents such as anastrozole, tamoxifen citrate, toremifene citrate, bicalutamide, flutamide and estramustine phosphate, platinum complexes such as carboplatin, cisplatin (CDDP) and nedaplatin, angiogenic inhibitors such as thalidomide, neovastat and bevacizumab and L-asparaginase.

When the active component in each of the agents, compositions and treatment method of the present invention described in the present Description is a nucleic acid such as an RNAi molecule, a ribozyme, an antisense nucleic acid or a DNA/RNA chimera polynucleotide, these may be used directly as a naked nucleic acid or may also be supported by various vectors. For the vector, any of the known vectors such as plasmid vectors, phage vectors, phagemid vectors, cosmid vectors, virus vectors can be employed. The vector preferably contains at least a promotor enhancing the expression of the nucleic acid to be supported, and the nucleic acid in this case is preferably ligated operably to a promoter. The nucleic acid ligated operably to a promotor means that the nucleic acid and the promoter are positioned so that the protein encoded by the nucleic acid can be suitably produced by the action of promoter. The vector may or may not be replicable in a host cell, and the gene transcription may be carried out outside or inside the nucleus in the host cell. In the latter case, the nucleic acid may be incorporated into the genome of the host cell.

Additionally, the active ingredient can also be supported by various nonviral lipid or protein carriers. Such a carrier is not limited and examples include cholesterols, liposomes, antibody promoters, cyclodextrin nanoparticles, fused peptides, aptamers, biodegradable polylactic acid copolymers and polymers, by which the intracellular incorporation efficiency can be increased (for example, see Pirollo and Chang, Cancer Res. 2008; 68(5):1247-50, etc.). Cationic liposomes and polymers (for example, polyethyleneimine, etc.) are particularly useful. Further examples of the useful polymer as such a carrier include those described in US 2008/0207553 and US 2008/0312174.

For each pharmaceutical composition of the present invention described in the present Description, the active component may be combined with other optional components as long as the effects of active component are not affected. Examples of the optional component include other chemotherapeutic agents, pharmacologically acceptable carriers, excipients and diluents. Further, depending on the administration route and drug release manner, the above composition may also be coated with a suitable material, for example, an enteric coating or a timed disintegrating material, or incorporated into a suitable drug release system.

Each agent and composition (including each pharmaceutical composition) of the present invention described in the present Description may be administered via various routes including both oral and parenteral, and examples of the administration route include, but not limited thereto, oral, intravenous, intramuscular, subcutaneous, local, intratumoral, intrarectal, intraarterial, intraportal, intraventricular, transmucosal, transdermal, intranasal, intraperitoneal, intrapulmonary and intrauterine, or may be prepared into a dosage form suitable for each administration route. Any known dosage form and preparation method can suitably be employed (for example, see "Hyojun Yakuzaigaku ("Standard Pharmaceutics" in English), edited by Yoshiteru Watanabe et al., Nankodo, 2003, etc.).

The dosage form suitable for oral administration is not limited and examples include powders, granules, tablets, capsules, solutions, suspensions, emulsions, gels and syrups, and examples of the dosage from suitable for parenteral administration include injections such as solution injections, suspension injections, emulsion injections and extemporaneously prepared injections. The parenteral administration preparation may be in the form of an aqueous or nonaqueous isotonic sterile solution or suspension.

Each agent or composition (including each pharmaceutical composition) of the present invention described in the present Description may also target a specific tissue or a cell. Targeting can be achieved by any known technique. When it is intended to deliver to a cancer, examples of the techniques usable include, but not limited thereto, the passive targeting in which the preparation is preferably sized to a diameter of 50 to 200 nm, particularly 75 to 150 nm, for producing EPR (enhanced permeability and retention) effects and the active targeting in which a ligand such as CD19, HER2, transferrin receptor, folic acid receptor, VIP receptor, EGFR (Torchilin, AAPS J. 2007; 9(2): E128-47), RAAG10 (JP Patent Publication (Kohyo) No. 2005-532050), PIPA (JP Patent Publication (Kohyo) No. 2006-506071) or KID3 (JP Patent Publication (Kohyo) No. 2007-529197), a peptide having a RGD motif or an NGR motif, F3 or LyP-1 (Ruoslahti et al., J Cell Biol. 2010; 188(6):759-68) is utilized as a targeting agent. Further, retinoid and a derivative thereof are also known to be useful as a targeting agent to a cancer cell (WO 2008/120815) and thus a carrier containing retinoid as a targeting agent can also be utilized. The carriers are described in WO2009/036368, WO 2010/014117 and WO 2012/170952 in addition to the above literatures.

Each agent or composition (including each pharmaceutical composition) of the present invention described in the present Description may be supplied in any form and, from the viewpoint of storage stability, may be provided in an extemporaneously preparable form such as the form preparable at a medical site or near the site by a doctor and/or a pharmacist, nurse or other paramedicals. Such a form is particularly useful when the agent or the composition of the present invention contains components that are difficult to store stably such as lipids, proteins and nucleic acids. In this case, the agent or the composition of the present invention is provided in 1 or 2 or more containers containing at least one element essential thereto and prepared before use, for example, within 24 hours, preferably before 3 hours, more preferably immediately before use. For the preparation, a reagent, a solvent and preparation equipment commonly available at a preparation site can be suitably used.

Thus, the present invention relates to a composition preparation kit including 1 or 2 or more containers containing the active components, which can be contained in each agent or composition of the present invention, singly or in combination and also essential elements of each agent or composition to be provided in the form of such a kit. The kit of the present invention may include, in addition to the above, instructions describing the preparation method and administration method of each agent or composition of the present invention such as written information and digital storage medium like CD or DVD. Additionally, the kit of the present invention may include all essential elements to complete each agent or composition of the present invention but does not always need to include all the elements. Thus, the kit of the present invention may not include a reagent and a solvent commonly available at medical sites and experiment facilities such as sterilized water, physiological saline and glucose solution.

The effective amount in each treatment method of the present invention described in the present Description is, for example, an amount that alleviates a symptom of a disease or delays or stops the progress of a disease, preferably an amount that suppresses or recovers a disease. Additionally, an amount not causing detrimental effects which outweighs the benefits gained from the administration is preferable. Such an amount is suitably determined by an in vitro test using cultured cells or a test on a model animal such as a mouse, a rat, a dog or a pig, and these test methods are well known by those skilled in the art. The dose of drug used in the treatment method of the present invention is known by those skilled in the art or can be suitably determined by the above tests.

The specific dose of active component administered in the treatment method of the present invention described in the present Description can be determined considering various conditions of a subject in need of the treatment such as severity degree of symptoms, general health conditions of a subject, age, body weight, sex of a subject, diet, administration timing and frequency, coadministered drugs, reactivity to the therapy, dosage form and compliance to the therapy.

The administration route includes various routes including both oral and parenteral such as oral, intravenous, intramuscular, subcutaneous, local, intratumoral, intrarectal, intraarterial, intraportal, intraventricular, transmucosal, transdermal, intranasal, intraperitoneal, intrapulmonary and intrauterine.

The administration frequency varies depending on the property of the agent or composition used and the conditions of a subject including the above but may be, for example, multiple times a day (more specifically, twice, 3, 4 times or 5 times or more a day), once a day, every several days (more specifically, every 2, 3, 4, 5, 6 or 7 days), every week, every several weeks (more specifically, every 2, 3 or 4 weeks).

The term "subject" used in the present Description means any biological individual, preferably animals, further preferably mammals, further preferably human individuals. In the present invention, the subject may be healthy or affected with a disease but when a treatment for a specific disease is intended, the subject typically means a subject who is affected or susceptible to be affected with the disease.

Additionally, the term "treatment", when used in the present Description, encompasses medically acceptable all kind of preventive and/or therapeutic intervention for the purpose of recovery, temporary remission or prevention of a disease. For example, the term "treatment" encompasses medically acceptable interventions with various purposes including delaying or stopping the progress of a disease, regressing or disappearing a lesion, preventing the onset or preventing the recurrence.

The drug suppressing GST-π demonstrates the cell death induction and/or the cell growth suppression for a cell having a mutation in the BRAF gene as described above. Thus, with the suppression of GST-π being an indicator, the cell death inducing agent and/or the cell growth suppressing agent for a cell having a mutation in the BRAF gene can be screened for. More specifically, a substance capable of suppressing GST-π can be a candidate substance for the cell death inducing agent and/or the cell growth suppressing agent for a cell having a mutation in the BRAF gene (typically, cancer cells).

For example, a test substance is contacted with a cancer cell having a mutation in the BRAF gene, as an example of the cancer cell, to measure an expression level of GST-π in the cell. When the expression level in the case of contact with the test substance is reduced compared with the expression level measured in the absence of the test substance, the test substance can be selected as a candidate substance for the drug suppressing GST-π.

The test substance herein is not limited and may be any substance. The test substance may be a single substance or a mixture consisting of a plurality of constituting components. The test substance may have a composition containing unidentified substances like an extract from a microorganism or a culture broth or a composition containing known compositions in a predetermined composition ratio. Additionally, the test substance may be any of proteins, nucleic acids, lipids, polysaccharides, organic compounds and inorganic compounds.

EXAMPLE

Hereinafter, the present invention is described further in detail with reference to examples, but the technical scope of the present invention is not limited thereto.

Example 1

In the present Example, the cell growth suppressing effect was studied when the drug suppressing GST-π was allowed to act on a cell having a mutation in the BRAF gene. First, as the cancer cell having a mutation (V600E) in the BRAF gene, 1 species of a colorectal cancer cell line (CACO-2) and 4 species of melanoma cell lines (A375, SK-MEL-28, A2058, Malme-3M) were cultured at 37° C. under the atmosphere containing 5% $CO_2$. The medium used were MEM+20%, FBS+0.1 mM and NEAA for CACO-2, DMEM+15% and FBS for A375, EMEM+10% and FBS for SK-MEL-28, DMEM+10% and FBS for A2058 and IMDM+20% and FBS for Malme-3M, to all of which an antibiotic was added.

On the day before the transfection, each cell was inoculated into a 100 mm-plastic tissue culture dish using antibiotic free medium so that 10 to 20% confluent was achieved. 600 pmol of GST-π siRNA (GGGAGGCAAGAC-CUUCAUUTT, siRNA ID#2385, Ambion (SEQ ID NO: 3)) was added to a 1 mL of Opti-MEM I Reduced Serum Medium (GIBCO) and gently mixed. Subsequently, 35 μL of Lipofectamine RNAi MAX (Invitrogen) was diluted with 1 mL of Opti-MEM I Reduced Serum Medium (GIBCO) and gently mixed. The diluted GST-π siRNA and the diluted Lipofectamine RNAi MAX were gently mixed and then incubated at room temperature for 10 minutes. Meanwhile, the medium was replaced with 10 mL of Opti-MEM I Reduced Serum Medium. After the 10-minute incubation, the complex of GST-π siRNA and Lipofectamine RNAi MAX was added to the cell and incubated at 37° C. under the atmosphere containing 5% $CO_2$. After the 5-hour incubation, the medium was replaced with 10 mL of antibiotic free medium. The medium was washed with PBS 1 hour after the replacement, the cells were peeled using 0.25% Trypsin-EDTA (SIGMA) and suspended in medium containing an antibiotic. The cells were suspended in 5 mL of medium and inoculated in a 60 mm-plastic tissue culture dish (CACO-2: $0.4 \times 10^5$ cells, A375: $1.0 \times 10^5$ cells, SK-MEL-28: $0.2 \times 10^5$ cells, A2058: $0.8 \times 10^5$ cells, Malme-3M: $0.6 \times 10^5$ cells).

The same operation was carried out as control experiments using Scramble siRNA (CGAUUCGCUAGACCG-GCUUCAUUGCAG, Hokkaido System Science Co., Ltd. (SEQ ID NO: 4)) or AllStars Negative Control siRNA (siControl) (QIAGEN). After the transfection of GST-π siRNA, the cell numbers was counted on Day 0 and Day 5, respectively.

Additionally, in the present Example, the expression of GST-π was confirmed by Western blotting respectively when GST-π siRNA was allowed to act on CACO-2 cells, A375 cells, SK-MEL-28 cells, A2058 cells and Malme-3M cells. More specifically, using the cell collected 3 days after the transfection of GST-π siRNA, the Western blotting analysis on GST-π knockdown was carried out. The collected cells were first washed with cold PBS, to which cold lysis buffer (1% NP-40, 50 mM Tris-HCl (pH 7.4), 150 mM NaCl, 1 mM EDTA, complete Mini EDTA-free (Roche) and PhosSTOP (Roche)) were added, ice-cooled and incubated for 30 minutes to solubilize. Subsequently, the centrifugation was carried out at 4° C., 15000 rpm for 15 minutes, thereby obtaining a cell extract. Proteins were quantitatively determined for the obtained cell extract using Micro BCA Protein Assay Kit (Thermo SCIENTIFIC). Next, 20 µg of the cell extract was denatured under reduction condition and SDS-PAGE was carried out using MULTIGEL II mini 4/20 (13 W) (Cosmo Bio) to separate proteins. After completion of SDS-PAGE, the proteins were transcribed to a PVDF membrane using a tank blotting apparatus. The transfer membrane was incubated in PBS with 5% skim milk/0.05% Tween 20 (abbreviated as PBS-T) at 4° C. for 16 hours to carry out the blocking. Subsequently, the membrane was reacted to an anti-GST-π (MBL) diluted with Membrane blocking Solution (Invitrogen) at 4° C. for 16 hours. The secondary antibody reaction was carried out at room temperature for 1 hour using a rabbit antibody labelled with horseradish peroxidase (HRP). The band signal detection was carried out on an X-ray film by the chemiluminescence method using ECL Western Blocking Detection Reagents (GE Healthcare). Washing between each of the operations was carried out by shaking for 5 minutes, 4 times using PBS-T.

Figure 2:
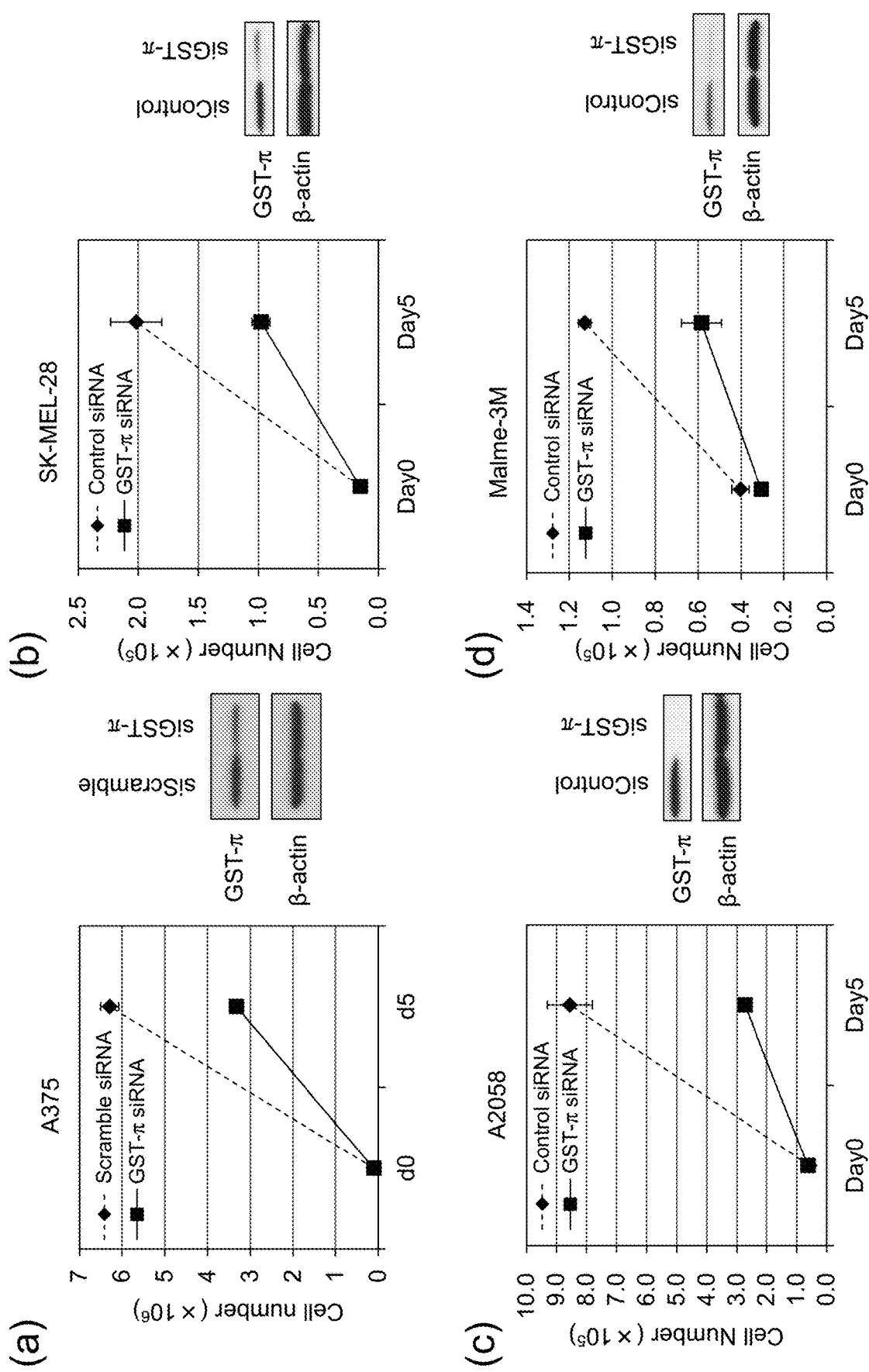
FIG. 2 are characteristic diagrams showing the verification results of cell growth suppressing effect due to GST-π knockdown in a melanoma cell line having a mutation in the BRAF gene (cell number count results, Western blotting results).

The results on the colorectal cancer cell line are shown in FIG. 1 and the results on the melanoma cell line are shown in FIG. 2. Note that FIGS. 1 and 2 together show the results of cell number counts and the results of Western blotting analysis. As appeared in FIGS. 1 and 2, both in the colorectal cancer cell line and the melanoma cell line, the cell growth ability was notably suppressed due to the GST-π knockdown by GST-π siRNA, which is the drug suppressing GST-π, in the cancer cells having a mutation in the BRAF gene. The mutation in the BRAF gene was found in highly malignant tumors and is known, in colorectal cancers, as the poor prognosis factor in irremovable colorectal cancers. A half of the melanoma patients have mutations in the BRAF gene and when a metastatic potential is high, the fatality and malignancy are the highest. The results of the present Example suggest that the drug suppressing GST-π is effective on the cell growth suppression of cancer cells having a mutation in the BRAF gene, thus raising expectations for a novel therapy on these intractable cancers.

Example 2

In the present Example, the cell growth suppressing effect was studied when the drug suppressing GST-π and a BRAF inhibitor were allowed to act on a cell having a mutation in the BRAF gene.

First, 1 species of a colorectal cancer cell line (CACO-2) and 2 species of melanoma cell lines (SK-MEL-28 and A2058) were respectively cultured in the same manner as in Example 1, and, on the day before the transfection, inoculated into a 100 mm-plastic tissue culture dish using antibiotic free medium so that 10 to 20% confluent was achieved. 600 pmol of GST-π siRNA (GGGAGGCAAGAC-CUUCAUUTT, siRNA ID#2385, Ambion (SEQ ID NO: 3)) was added to 1 mL of Opti-MEM I Reduced Serum Medium (GIBCO) and gently mixed. Subsequently, 35 µL of Lipofectamine RNAi MAX (Invitrogen) was diluted with 1 mL of Opti-MEM I Reduced Serum Medium (GIBCO) and gently mixed. The diluted GST-π siRNA and the diluted Lipofectamine RNAi MAX were gently mixed and then incubated at room temperature for 10 minutes. Meanwhile, the medium was replaced with 10 mL of Opti-MEM I Reduced Serum Medium. After the 10-minute incubation, the complex of GST-π siRNA and Lipofectamine RNAi MAX was added to the cell and incubated at 37° C. under the atmosphere containing 5% $CO_2$. After the 5-hour incubation, the medium was replaced with 10 mL of antibiotic free medium. The medium was washed with PBS 1 hour after the replacement, the cells were peeled using 0.25% Trypsin-EDTA (SIGMA) and suspended in medium containing an antibiotic. The cells were suspended in 5 mL of medium and inoculated in a 60 mm-plastic tissue culture dish (CACO-2: $0.4 \times 10^5$ cells, SK-MEL-28: $0.2 \times 10^5$ cells and A2058: $0.8 \times 10^5$ cells). The same operation was carried out as a control experiment using AllStars Negative Control siRNA (siControl) (QIAGEN). On Day 1 from the transfection, PLX4720 (Selleck), a BRAF inhibitor, was added to medium so as to achieve 40 µM for CACO-2, 0.7 µM for SK-MEL-28 and 10 µM for A2058 and culture was continued to Day 5. The PLX4720-treated control was cultured by adding a DMSO (Wako Pure Chemical Industries, Ltd.) solvent. Growth assay was carried out by counting the cell numbers from Day 0 to Day 5 after the transfection.

Figure 3:
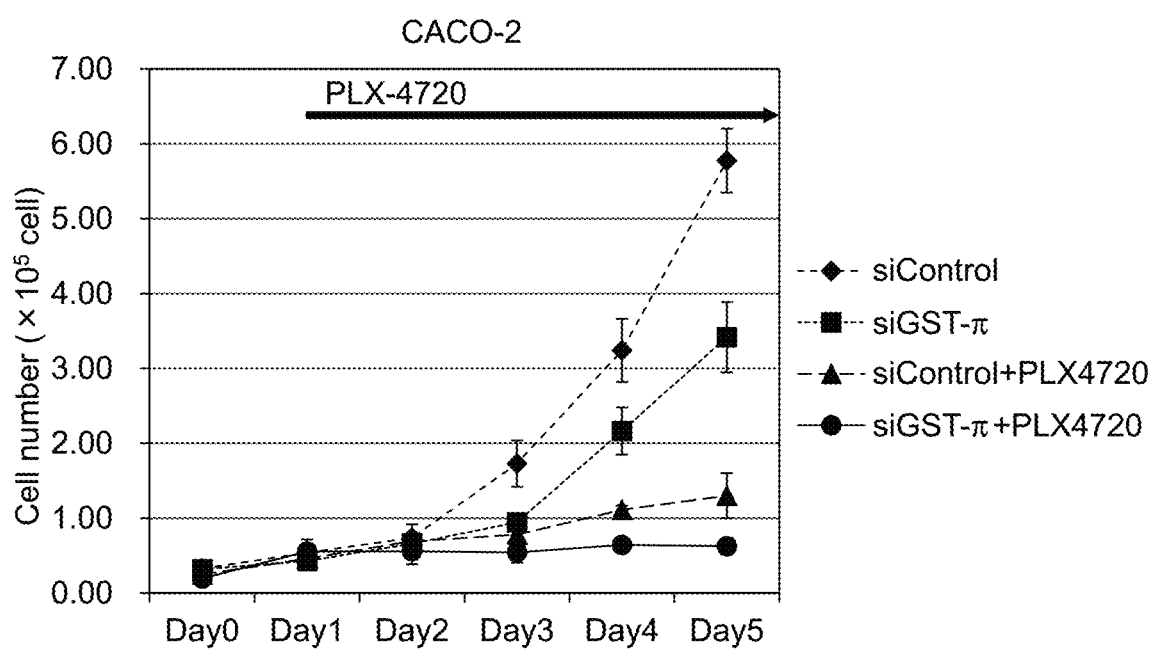
FIG. 3 is a characteristic diagram showing the verification results of cell growth suppressing effect when GST-π siRNA and a BRAF inhibitor were used in combination in a colorectal cancer cell line having a mutation in the BRAF gene.
Figure 4:
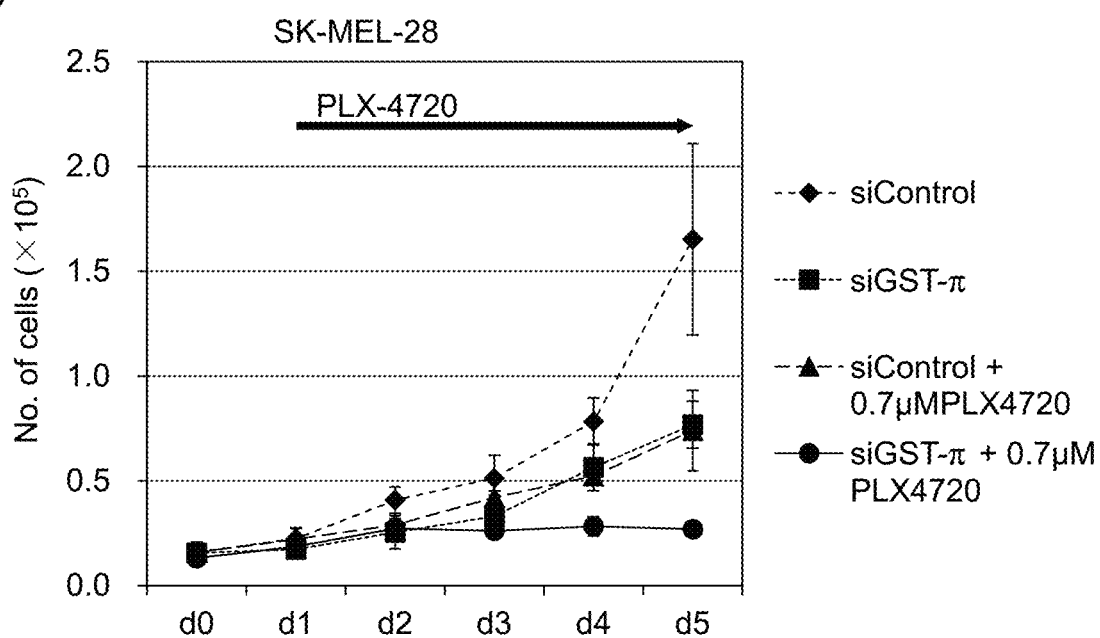
FIG. 4 are characteristic diagrams showing the verification results of cell growth suppressing effects when GST-π siRNA and a BRAF inhibitor were used in combination in a melanoma cell line having a mutation in the BRAF gene.
Figure 4:
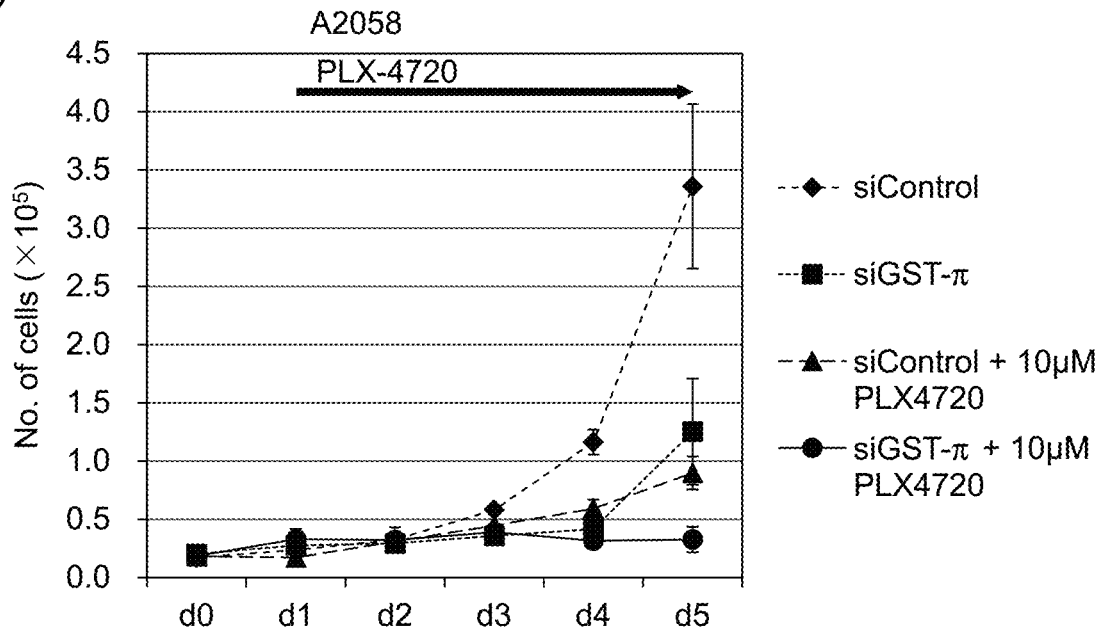

FIG. 3 shows the result on the cell number count of CACO-2 and FIG. 4 shows the results on the cell number counts of SK-MEL-28 and A2058. As evident in FIG. 3, it was suggested that, in comparison with the case where GST-π siRNA was allowed to act singly on the colorectal cancer cell line (CACO-2 line having a mutation in the BRAF gene) or the case where PLX4720 was allowed to act on the colorectal cancer cell line together with siControl, the cell growth suppressing effect was remarkable in the case where GST-π siRNA and PLX4720 were allowed to act in combination on such a cell line. Further, as evident in FIG. 4, it was suggested that, in comparison with the case where GST-π siRNA was allowed to act singly on the melanoma cell lines (SK-MEL-28 and A2058 having a mutation in the BRAF gene) or the case where PLX4720 was allowed to act on the melanoma cell lines together with siControl, the cell growth suppressing effect was remarkable in the case where GST-π siRNA and PLX4720 were allowed to act in combination on such melanoma cell lines.

Example 3

In the present Example, the cell growth suppressing effect was studied when the drug suppressing GST-π was allowed to act on a cell having a mutation in the BRAF gene and resistance to a BRAF inhibitor (BRAF inhibitor resistant cell).

<Cell Number Count>

The BRAF inhibitor resistant cell used in the present Example was produced as follows. The melanoma cell line A375 used in Example 1 was incubated in DMEM medium containing an antibiotic to which 1 to 5 µM of PLX4720 (Selleck) was added and 15% FBS at 37° C. under the atmosphere containing 5% $CO_2$ for a month. The cell line survived after 1-month incubation was determined as the PLX4720 resistant A375 cells and used in the present Example.

In the present Example, on the day before the transfection, PLX4720 resistant A375 cell was inoculated into a 100 mm-plastic tissue culture dish using antibiotic free DMEM medium containing 15% FBS so that $0.5 \times 10^6$ cells/10 ml was achieved. 600 pmol of GST-π siRNA (GGGAG- GCAAGACCUUCAUUTT, siRNA ID#2385, Ambion (SEQ ID NO: 3)) was added to 1 mL of Opti-MEM I Reduced Serum Medium (GIBCO) and gently mixed. Subsequently, 35 μL of Lipofectamine RNAi MAX (Invitrogen) was diluted with 1 mL of Opti-MEM I Reduced Serum Medium (GIBCO) and gently mixed. The diluted GST-π siRNA and the diluted Lipofectamine RNAi MAX were gently mixed and then incubated at room temperature for 10 minutes. Meanwhile, the medium was replaced with 10 mL of Opti-MEM I Reduced Serum Medium. After the 10-minute incubation, the complex of GST-π siRNA and Lipofectamine RNAi MAX was added to the cell and incubated at 37° C. under the atmosphere containing 5% $CO_2$. After the 5-hour incubation, the medium was replaced with 10 mL of antibiotic free DMEM medium containing 15% FBS. The medium was washed with PBS 2 hours after the replacement, the cells were peeled using 0.5% Trypsin-EDTA (SIGMA) and suspended in DMEM medium containing an antibiotic and 15% FBS. The cells in the suspension were inoculated in a 60 mm-plastic tissue culture dish so that $1.0 \times 10^5$ cells/5 ml was achieved. The same operation was carried out as control experiments using Scramble siRNA (CGAUUCGCUAGACCGGCUUCAUUGCAG, Hokkaido System Science Co., Ltd. (SEQ ID NO: 4)) or AllStars Negative Control siRNA (QIAGEN). After the transfection of GST-π siRNA, the cell number was counted on Days 0, 1, 2, 3, 4 and 5, respectively.

<GST-π Expression Confirmation>

The expression of GST-π was confirmed by Western blotting when GST-π siRNA was allowed to act on PLX4720 resistant A375 cell as described above. More specifically, using the cells collected on each of the above times after the transfection of GST-π siRNA, Western blotting analysis on GST-π knockdown was carried out.

The collected cells were first washed with cold PBS, to which cold lysis buffer (1% NP-40, 50 mM Tris-HCl (pH 7.4), 150 mM NaCl, 1 mM EDTA, complete Mini EDTA-free (Roche) and PhosSTOP (Roche)) were added, ice-cooled and incubated for 30 minutes to solubilize. The centrifugation was carried out at 4° C., 15000 rpm for 15 minutes, thereby obtaining a cell extract. Proteins were quantitatively determined for the obtained cell extract using Micro BCA Protein Assay Kit (Thermo SCIENTIFIC). Next, 20 mg of the cell extract was denatured under reduction condition and SDS-PAGE was carried out using MULTIGEL II mini 4/20 (13 W) (Cosmo Bio) to separate proteins. After completion of SDS-PAGE, the proteins were transcribed to a PVDF membrane using a tank blotting apparatus. The transfer membrane was incubated in PBS with 5% skim milk/0.05% Tween 20 (abbreviated as PBS-T) at 4° C. for 16 hours to carry out the blocking. Subsequently, the membrane was reacted to an anti-GST-π (MBL) diluted with Membrane blocking Solution (Invitrogen) at 4° C. for 16 hours. The secondary antibody reaction was carried out at room temperature for 1 hour using a rabbit antibody labelled with horseradish peroxidase (HRP). The band signal detection was carried out on an X-ray film by the chemiluminescence method using ECL Western Blocking Detection Reagents (GE Healthcare). Washing between each of the operations was carried out by shaking for 5 minutes, 4 times using PBS-T.

<Result>

Figure 5:
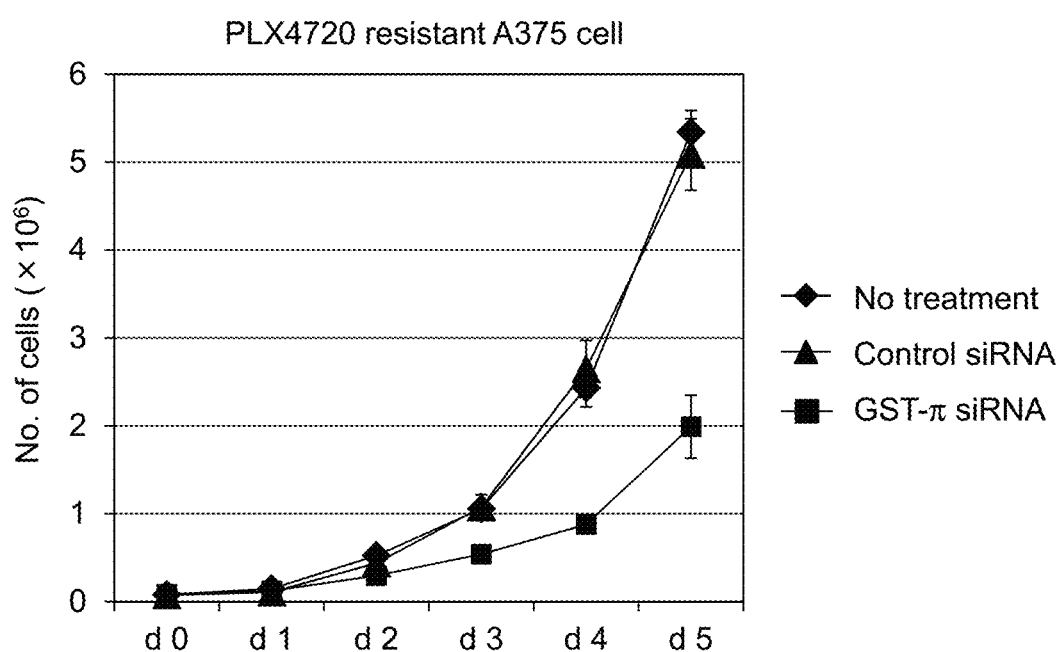
FIG. 5 is a characteristic diagram showing the verification results of cell growth suppressing effect due to GST-π knockdown in a melanoma cell line having a mutation in the BRAF gene and resistant to a BRAF inhibitor.
Figure 6:
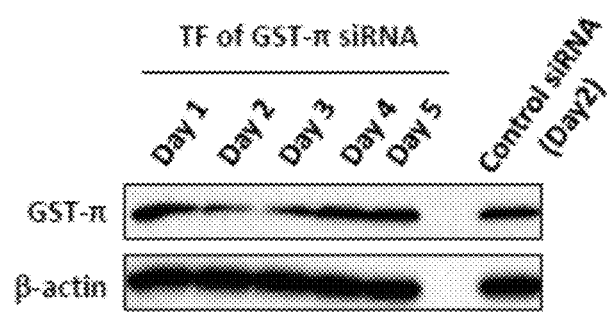
FIG. 6 are electrophoresis photographs showing the results of Western blotting analysis on GST-π expression when GST-π was knocked down in a melanoma cell line having a mutation in the BRAF gene and resistant to a BRAF inhibitor.

In recent years, the melanoma cell line acquired the BRAF inhibitor resistance is understood to be involved with the recurrence of melanoma. Accordingly, GST-π was knocked down using PLX4720 resistant A375 to investigate whether GST-π facilitates the CRAF dependency in the BRAF inhibitor resistant melanoma. The measurement of cell growth revealed the notable growth suppressing effect (FIG. 5). When the GST-π knockdown was confirmed, the GST-π expression was suppressed on Day 2 and Day 3 (FIG. 6).

The present Example suggests that the growth of cells having a mutation in the BRAF gene and resistance to a BRAF inhibitor (BRAF inhibitor resistant cell) was effectively suppressed. According to the results, the effect to prevent or reduce diseases in which the BRAF inhibitor resistant cell is a factor, for examples, the recurrence of melanoma, can be expected.

All publications, patents and patent applications cited herein shall be incorporated per se in the present Description by reference.

The invention claimed is:

1. A method for inducing cell death for a cell having a mutation in a BRAF gene, comprising a step of contacting a drug suppressing GST-π with the cell having a mutation in a BRAF gene, wherein the cell having a mutation in a BRAF gene is a cell resistant to a BRAF inhibitor.

2. A method for suppressing cell growth for a cell having a mutation in a BRAF gene, comprising a step of contacting a drug suppressing GST-π with the cell having a mutation in a BRAF gene, wherein the cell having a mutation in a BRAF gene is a cell resistant to a BRAF inhibitor.

3. The method according to claim 1 or 2, wherein the mutation is V600E mutation.

4. The method according to claim 1 or 2, wherein the drug is a substance selected from the group consisting of RNAi molecules, ribozymes, antisense nucleic acids, DNA/RNA chimera polynucleotides and vectors expressing at least one thereof.

5. The method according to claim 1 or 2, wherein the cell having a mutation in a BRAF gene is a cancer cell highly expressing GST-π.

6. A method for treating a disease caused by a growth defect of a cell having a mutation in a BRAF gene, comprising a step of administering a drug suppressing GST-π, wherein the cell having a mutation in a BRAF gene is a cell resistant to a BRAF inhibitor.

7. The method according to claim 6, wherein the disease is a cancer.

8. The method according to claim 7, wherein the cancer is a cancer highly expressing GST-π.

9. The method according to claim 7, wherein the cancer is colorectal cancer or melanoma.

10. The method according to claim 1 or 2, wherein the cell is a colorectal cancer cell.

11. The method according to claim 7, wherein the cancer is colorectal cancer.

* * * * *

UNITED STATES PATENT AND TRADEMARK OFFICE
CERTIFICATE OF CORRECTION

PATENT NO. : 10,570,396 B2
APPLICATION NO. : 15/567062
DATED : February 25, 2020
INVENTOR(S) : Yoshiro Niitsu et al.

Page 1 of 1

It is certified that error appears in the above-identified patent and that said Letters Patent is hereby corrected as shown below:

In the Specification

In Column 6, Line 19, "Nothern" should be --Northern--.

In Column 10, Line 54, "oteracyl" should be --oteracil--.

In Column 18, Line 4, "mg" should be --µg--.

Signed and Sealed this
Eighteenth Day of August, 2020

Andrei Iancu
*Director of the United States Patent and Trademark Office*

SEQUENCE LISTING

```
<160> NUMBER OF SEQ ID NOS: 4

<210> SEQ ID NO 1
<211> LENGTH: 986
<212> TYPE: DNA
<213> ORGANISM: Homo sapiens
<220> FEATURE:
<221> NAME/KEY: CDS
<222> LOCATION: (250)..(882)

<400> SEQUENCE: 1
tgggaaagag ggaaaggctt ccccggccag ctgcgcggcg actccgggga ctccagggcg      60
cccctctgcg gccgacgccc ggggtgcagc ggccgccggg gctggggccg gcgggagtcc     120
gcgggaccct ccagaagagc ggccggcgcc gtgactcagc actggggcgg agcggggcgg     180
gaccaccctt ataaggctcg gaggccgcga ggccttcgct ggagtttcgc cgccgcagtc     240 ttcgccacc atg ccg ccc tac acc gtg gtc tat ttc cca gtt cga ggc cgc     291
         Met Pro Pro Tyr Thr Val Val Tyr Phe Pro Val Arg Gly Arg
           1               5                  10 tgc gcg gcc ctg cgc atg ctg ctg gca gat cag ggc cag agc tgg aag     339
Cys Ala Ala Leu Arg Met Leu Leu Ala Asp Gln Gly Gln Ser Trp Lys
 15                  20                  25                  30
```

| | | | | | | | | | | | | | | | | |
|---|---|---|---|---|---|---|---|---|---|---|---|---|---|---|---|---|
| gag | gag | gtg | gtg | acc | gtg | gag | acg | tgg | cag | gag | ggc | tca | ctc | aaa | gcc | 387 |
| Glu | Glu | Val | Val | Thr | Val | Glu | Thr | Trp | Gln | Glu | Gly | Ser | Leu | Lys | Ala | |
| | | | | 35 | | | | | 40 | | | | | 45 | | |
| tcc | tgc | cta | tac | ggg | cag | ctc | ccc | aag | ttc | cag | gac | gga | gac | ctc | acc | 435 |
| Ser | Cys | Leu | Tyr | Gly | Gln | Leu | Pro | Lys | Phe | Gln | Asp | Gly | Asp | Leu | Thr | |
| | | | | 50 | | | | | 55 | | | | | 60 | | |
| ctg | tac | cag | tcc | aat | acc | atc | ctg | cgt | cac | ctg | ggc | cgc | acc | ctt | ggg | 483 |
| Leu | Tyr | Gln | Ser | Asn | Thr | Ile | Leu | Arg | His | Leu | Gly | Arg | Thr | Leu | Gly | |
| | | | | 65 | | | | | 70 | | | | | 75 | | |
| ctc | tat | ggg | aag | gac | cag | cag | gag | gca | gcc | ctg | gtg | gac | atg | gtg | aat | 531 |
| Leu | Tyr | Gly | Lys | Asp | Gln | Gln | Glu | Ala | Ala | Leu | Val | Asp | Met | Val | Asn | |
| | | | 80 | | | | | 85 | | | | | 90 | | | |
| gac | ggc | gtg | gag | gac | ctc | cgc | tgc | aaa | tac | atc | tcc | ctc | atc | tac | acc | 579 |
| Asp | Gly | Val | Glu | Asp | Leu | Arg | Cys | Lys | Tyr | Ile | Ser | Leu | Ile | Tyr | Thr | |
| 95 | | | | | 100 | | | | | 105 | | | | | 110 | |
| aac | tat | gag | gcg | ggc | aag | gat | gac | tat | gtg | aag | gca | ctg | ccc | ggg | caa | 627 |
| Asn | Tyr | Glu | Ala | Gly | Lys | Asp | Asp | Tyr | Val | Lys | Ala | Leu | Pro | Gly | Gln | |
| | | | | 115 | | | | | 120 | | | | | 125 | | |
| ctg | aag | cct | ttt | gag | acc | ctg | ctg | tcc | cag | aac | cag | gga | ggc | aag | acc | 675 |
| Leu | Lys | Pro | Phe | Glu | Thr | Leu | Leu | Ser | Gln | Asn | Gln | Gly | Gly | Lys | Thr | |
| | | | 130 | | | | | 135 | | | | | 140 | | | |
| ttc | att | gtg | gga | gac | cag | atc | tcc | ttc | gct | gac | tac | aac | ctg | ctg | gac | 723 |
| Phe | Ile | Val | Gly | Asp | Gln | Ile | Ser | Phe | Ala | Asp | Tyr | Asn | Leu | Leu | Asp | |
| | | | | 145 | | | | | 150 | | | | | 155 | | |
| ttg | ctg | ctg | atc | cat | gag | gtc | cta | gcc | cct | ggc | tgc | ctg | gat | gcg | ttc | 771 |
| Leu | Leu | Leu | Ile | His | Glu | Val | Leu | Ala | Pro | Gly | Cys | Leu | Asp | Ala | Phe | |
| | | | 160 | | | | | 165 | | | | | 170 | | | |
| ccc | ctg | ctc | tca | gca | tat | gtg | ggg | cgc | ctc | agt | gcc | cgg | ccc | aag | ctc | 819 |
| Pro | Leu | Leu | Ser | Ala | Tyr | Val | Gly | Arg | Leu | Ser | Ala | Arg | Pro | Lys | Leu | |
| 175 | | | | | 180 | | | | | 185 | | | | | 190 | |
| aag | gcc | ttc | ctg | gcc | tcc | cct | gag | tac | gtg | aac | ctc | ccc | atc | aat | ggc | 867 |
| Lys | Ala | Phe | Leu | Ala | Ser | Pro | Glu | Tyr | Val | Asn | Leu | Pro | Ile | Asn | Gly | |
| | | | | 195 | | | | | 200 | | | | | 205 | | |
| aac | ggg | aaa | cag | tga | gggttggggg | | gactctgagc | | gggaggcaga | | gtttgccttc | | | | | 922 |
| Asn | Gly | Lys | Gln | | | | | | | | | | | | | |
| | | | 210 | | | | | | | | | | | | | |
| ctttctccag | | gaccaataaa | | atttctaaga | | gagctaaaaa | | aaaaaaaaaa | | aaaaaaaaaa | | | | | | 982 |
| aaaa | | | | | | | | | | | | | | | | 986 |

<210> SEQ ID NO 2
<211> LENGTH: 210
<212> TYPE: PRT
<213> ORGANISM: Homo sapiens

<400> SEQUENCE: 2

Met Pro Pro Tyr Thr Val Val Tyr Phe Pro Val Arg Gly Arg Cys Ala
1               5                   10                  15

Ala Leu Arg Met Leu Leu Ala Asp Gln Gly Gln Ser Trp Lys Glu Glu
            20                  25                  30

Val Val Thr Val Glu Thr Trp Gln Glu Gly Ser Leu Lys Ala Ser Cys
        35                  40                  45

Leu Tyr Gly Gln Leu Pro Lys Phe Gln Asp Gly Asp Leu Thr Leu Tyr
    50                  55                  60

Gln Ser Asn Thr Ile Leu Arg His Leu Gly Arg Thr Leu Gly Leu Tyr
65                  70                  75                  80

Gly Lys Asp Gln Gln Glu Ala Ala Leu Val Asp Met Val Asn Asp Gly
                85                  90                  95

```
Val Glu Asp Leu Arg Cys Lys Tyr Ile Ser Leu Ile Tyr Thr Asn Tyr
            100                 105                 110

Glu Ala Gly Lys Asp Asp Tyr Val Lys Ala Leu Pro Gly Gln Leu Lys
        115                 120                 125

Pro Phe Glu Thr Leu Leu Ser Gln Asn Gln Gly Gly Lys Thr Phe Ile
        130                 135                 140

Val Gly Asp Gln Ile Ser Phe Ala Asp Tyr Asn Leu Leu Asp Leu Leu
145                 150                 155                 160

Leu Ile His Glu Val Leu Ala Pro Gly Cys Leu Asp Ala Phe Pro Leu
                165                 170                 175

Leu Ser Ala Tyr Val Gly Arg Leu Ser Ala Arg Pro Lys Leu Lys Ala
                180                 185                 190

Phe Leu Ala Ser Pro Glu Tyr Val Asn Leu Pro Ile Asn Gly Asn Gly
            195                 200                 205

Lys Gln
    210

<210> SEQ ID NO 3
<211> LENGTH: 21
<212> TYPE: DNA
<213> ORGANISM: Artificial
<220> FEATURE:
<223> OTHER INFORMATION: Synthesize RNA

<400> SEQUENCE: 3
gggaggcaag accuucauut t                                          21

<210> SEQ ID NO 4
<211> LENGTH: 27
<212> TYPE: DNA
<213> ORGANISM: Artificial
<220> FEATURE:
<223> OTHER INFORMATION: Synthesize RNA

<400> SEQUENCE: 4
cgauucgcua gaccggcuuc auugcag                                    27
```